United States Patent [19]

Kamiguchi et al.

[11] Patent Number: 4,605,776

[45] Date of Patent: Aug. 12, 1986

[54] PROCESS FOR PRODUCING ACETONE

[75] Inventors: Taiji Kamiguchi; Mutsuo Yamada; Yoshijiro Arikawa; Takanori Kuwahara; Hirotoshi Tanimoto; Yasuyuki Nishimura; Hiroyuki Kaku, all of Kure, Japan

[73] Assignee: Babcock-Hitachi Kabushiki Kaisha, Tokyo, Japan

[21] Appl. No.: 694,099

[22] Filed: Jan. 23, 1985

[30] Foreign Application Priority Data

Jan. 27, 1984 [JP] Japan .................... 59-012144
Mar. 8, 1984 [JP] Japan .................... 59-044469

[51] Int. Cl.$^4$ .................................. C07C 45/35
[52] U.S. Cl. ........................................ 568/401
[58] Field of Search ........................ 568/400, 401

[56] References Cited

U.S. PATENT DOCUMENTS

| | | | |
|---|---|---|---|
| 3,365,498 | 1/1968 | Bryant et al. | 568/401 |
| 3,471,532 | 10/1968 | Young | 568/401 |
| 3,965,185 | 6/1976 | Young | 568/401 |
| 4,195,039 | 3/1980 | Mimoun et al. | 568/401 |
| 4,322,562 | 3/1982 | Toviog et al. | 568/401 |

*Primary Examiner*—James H. Reamer
*Attorney, Agent, or Firm*—Beall Law Offices

[57] ABSTRACT

A process for producing acetone selectively and with a high yield by oxidizing propylene by means of the combined oxygen in an oxygen complex under milder conditions and at a single stage is provided wherein a composite catalyst comprising as catalyst components, a transition metal complex with the metal ion of which oxygen molecule can coordinate to form an oxygen complex, and another kind transition metal complex with the metal ion of which propylene can coordinate to form a propylene complex is employed, and propylene activated by the complex formation is oxidized by the combined oxygen activated by the complex formation to thereby obtain acetone.

19 Claims, 2 Drawing Figures

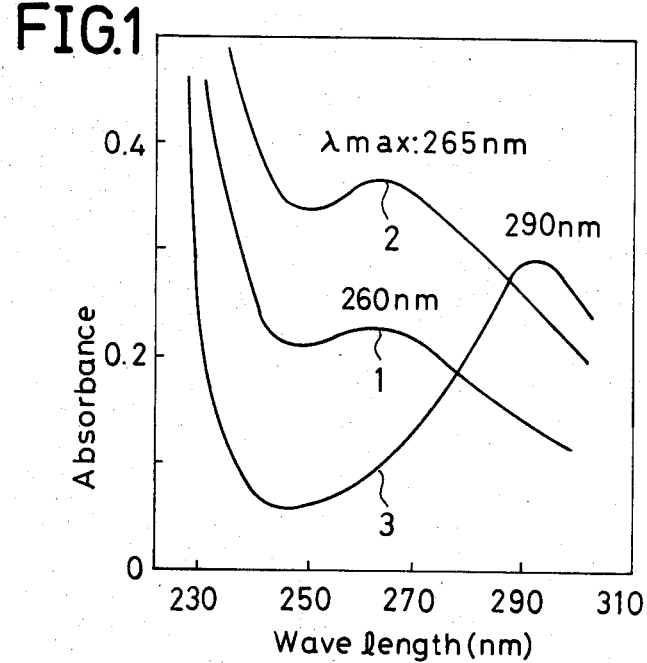
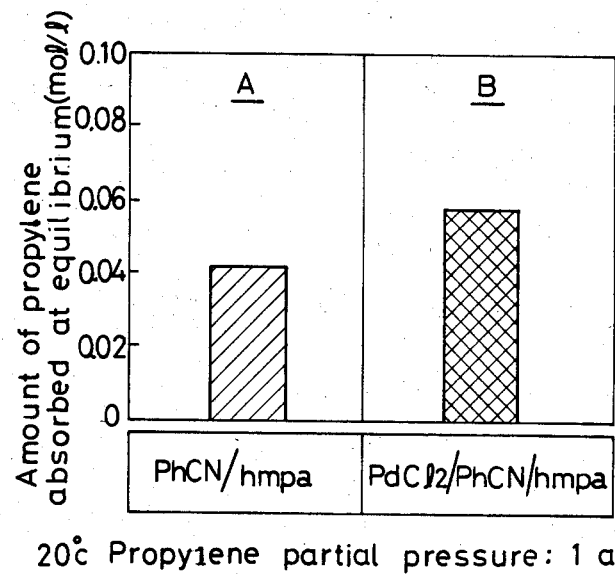

PROCESS FOR PRODUCING ACETONE

BACKGROUND OF THE INVENTION

This invention relates to a process for producing acetone and more particularly it relates to a process for producing acetone by oxidizing propylene by means of an oxygen complex.

Acetone is a representative aliphatic ketone and has been used not only commercially used as solvents for acetylcellulose, nitrocellulose, acetylene, etc. in a large amount, but also used as solvents for fats, resins, camphor, etc. in pharmaceutical field, and further as synthetic raw materials for many intermediate products such as methyl isobutyl ketone, methyl isobutyl carbinol, methyl methacrylate, bisphenol A and further ketene, etc.; thus it has occupied an important position in chemical industries.

The commercial process for producing acetone is roughly classified into the following ones: (1) isopropanol dehydrogenation process, (2) cumene process and (3) propylene oxidization process.

Isopropanol dehydrogenation process among these has been operated under severe conditions of 300°~500° C. and 3 atm in the presence of a dehydrogenation catalyst such as ZnO, Cu, etc. and the isopropanol conversion and the selectivity to acetone have been regarded as 98% and 90%, respectively (see Industrial Organic Chemistry, page 266, written by K. Weissermel and H. J. Arpe and translated by Teruaki Mukaiyama, Tokyo Kagaku Dojin (1978)). Further, cumene process is directed to a process wherein cumene is oxygen-oxidized at 120° C. and under the atmospheric pressure in liquid phase in the presence of Cu, Co salt or the like as catalyst to prepare cumene hydroperoxide, which is then decomposed with 0.1~2% $H_2SO_4$ at 60°~65° C. into phenol and acetone. The selectivity based on cumene is about 90% and the proportion of the products is 60% of phenol and 40% of acetone. These processes have been currently operated, but a process for producing acetone under milder reaction conditions and at a single stage has been noted, that is, the so-called Wacker process wherein propylene is used as raw material and palladium chloride ($Pd(2)Cl_2$)-cupric chloride ($Cu(2)Cl_2$) is employed as catalyst. This process is most characteristic among processes for producing acetone (see the above literature, page 265). According to this process, a composite catalyst obtained by dissolving $Pd(2)Cl_2$ and $Cu(2)Cl_2$ as catalyst in a hydrochloric acid solution (pH: 0~2) is employed. First propylene is oxidized by divalent palladium (Pd(2)) and water to form acetone ($CH_3COCH_3$). Water participates in this reaction as shown in the following equation:

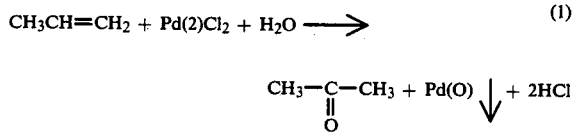

$$CH_3CH=CH_2 + Pd(2)Cl_2 + H_2O \longrightarrow \quad (1)$$

$$CH_3-\underset{\underset{O}{\parallel}}{C}-CH_3 + Pd(0)\downarrow + 2HCl$$

As seen from this reaction equation, Pd(2) is reduced into metal palladium (Pd(0)) which precipitates. It is necessary to prevent this and also oxidize Pd(0) into Pd(2) for regeneration by making a large amount of $Cu(2)Cl_2$ coexistent therewith, as shown in the following equation:

$$Pd(0)+2Cu(2)Cl_2\rightarrow Pd(2)Cl_2+2Cu(1)Cl \quad (2)$$

Further, difficultly soluble Cu(1)Cl byproduced at that time is oxygen-oxidized in the coexistence of HCl according to the following equation and returned to $Cu(2)Cl_2$:

$$2Cu(1)Cl+\tfrac{1}{2}O_2+2HCl\rightarrow 2CuCl_2+H_2O \quad (3)$$

As described above, by employing a redox system of Pd(2)/Pd(0) and Cu(2)/Cu(1), a continuous oxidation of propylene is made possible. However, since the oxygen molecule is not directly reacted with propylene, but a complicated oxidation-reduction reaction of the Pd(2)/Pd(0)—Cu(2)/Cu(1) system is utilized as described above, this constitutes a rate-determining step of the reaction. Further, since difficultly soluble Pd(0) and Cu(1)Cl are formed midway the reaction, a high concentration of HCl aqueous solution (pH: 0~2) is used and hence choice of a corrosion-resistant material is required. Still further, since the solubility of oxygen in water is low, its solubility must be raised, and since the higher the olefin, the lower the reactivity, the reaction conditions are as severe as 140° C. and 14 atm. In addition, it has been regarded that under such conditions, the conversion of propylene is 99% or higher, the selectivity to acetone is 92% and 2~4% of propionaldehyde is produced (see the above literature, page 265). Furthermore, if oxygen dissolved in excess is discharged into the gas phase, it is mixed with propylene and has a possibility of troubles such as explosion; hence a countermeasure thereto becomes necessary (Revised complete works of production flow sheet, edited by Kihara et al, Vol. II, p. 296, Kagaku Kogyosha (1978)).

As described above, any process has been carried out at relatively high temperatures and pressures; thus a process wherein acetone can be produced under milder conditions and at a single stage has been desired.

SUMMARY OF THE INVENTION

The object of the present invention is to solve these problems and provide a process for producing acetone selectively and with a high yield by oxidizing propylene by means of the combined oxygen in an oxygen complex under milder conditions and at a single stage.

In short, the present invention is directed to a process wherein a composite catalyst comprising as catalyst components, a transition metal complex with the metal ion of which oxygen molecule can coordinate to form an oxygen complex, and another kind transition metal complex with the metal ion of which propylene can coordinate to form a propylene complex, is employed, and propylene activated by the complex formation is oxidized by the combined oxygen activated by the complex formation to thereby obtain acetone under mild conditions in a non-aqueous solvent system.

Namely the present invention resides in a process for producing acetone by oxygen-oxidizing propylene in the presence of a metal complex catalyst, which process comprises employing a composite catalyst containing as the metal complex catalyst, a complex (Mm Xn.Ll) capable of forming an oxygen complex catalyst by coordination of the complex with oxygen and a complex (M'm'Xn'.L'Ll) capable of forming a propylene complex by coordination of the complex with propylene, wherein M means a transition metal belonging to the group I, the groups IV~VII or iron group in the group VIII of the Periodic Table; X, an anion such as halogens; L, an organic phosphorus compound; M', a transition metal belonging to platinum group in the group VIII of the Periodic Table; L', a coordinating compound selected from the group consisting of nitriles, and organic fluorine compounds; m, m', n and n', each a number determined by the valences of the above transition metals and the above anion; and l, l', each the number of ligands. The above m, m', n, n', l and l' are each preferably in the range of 1~4.

BRIEF DESCRIPTION OF THE DRAWINGS

FIG. 1 shows a view illustrating the ultraviolet absorption spectra of complexes employed in the present invention.

FIG. 2 shows a view illustrating the results of studies on the formation of propylene complex, according to gas absorption method.

DETAILED DESCRIPTION OF THE PREFERRED EMBODIMENTS

As to oxygen complexes capable of constituting an oxidizing agent effective for the oxidation reaction of various organic compounds, various studies have been made on copper heme-protein, iron heme-protein, etc. (Chemistry of Metal Proteins, edited by Ohtsuka and Yamanaka, Kohdansha (1983)). However, examples of oxidation reactions of organic substances by means of oxygen complexes, carried out on a commercial scale are very few.

The present inventors have made extensive research on stable oxygen complexes based on transition metal compounds, utilizable for oxidation of organic substrates. In a representative example, a solution of (Cu(1)Cl.hmpa), a complex of cuprous chloride (Cu(1)Cl) with hexamethylphosphoramide (other name: tris(dimethylamino)phosphine oxide; hereinafter denoted as hmpa) (Japanese patent application laid-open No. Sho 56-118720 (1981) and Sho 57-19013 (1982)) proposed as an absorbing solution for carbon monoxide (CO), exhibits a deep green color when contacted with oxygen.

Such a complex is expressed by the general formula Mm Xn.Ll. In the above case, M is Cu, X is Cl, L is hmpa, m=1, n=1 and l=1. Further, when Ti(3) or V(3) is a central metal and the anion is e.g. Cl⁻, the resulting complex is Ti(3)Cl₃.hmpa or V(3)Cl₃.hmpa (m=1, n=3 and l=1), respectively.

Now, when a solution of Cu(1) compound absorbs oxygen, monovalent copper of a lower valence is usually oxygen-oxidized into divalent copper as shown in the following equation; hence the present inventors initially considered that the same oxidation reaction might occur also in the Cu(1)Cl.hmpa solution and as a result its color might change to green color:

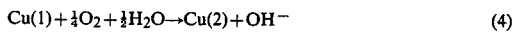
 (4)

However, the color of the complex solution of divalent copper compound (Cu(2)Cl₂) with hmpa was dark red; thus it was found that the oxidation reaction as described above did not occur. In order to further clarify this point, we measured the ultraviolet absorption spectra of the respective solutions. As a result it was found that as shown in FIG. 1, the spectra of the solution of Cu(1)Cl.hmpa complex (solvent: ethanol) (numeral 1 of FIG. 1) and the spectra of a solution obtained by having oxygen absorbed in the above complex solution (numeral 2 of FIG. 1) were entirely different from the spectra of the divalent copper complex (Cu(2)Cl₂.(hmpa)₂) solution (numeral 3 of FIG. 1). From these results, it was confirmed that in the case of Cu(1)Cl.hmpa solution, even when oxygen was absorbed, the oxygen was not consumed to oxidize Cu(1) in the solution into Cu(2), but it was present in the form of the so-called oxygen complex wherein it coordinated with Cu(1) in the form of oxygen molecule.

Definite concentrations of Cu(1)Cl.hmpa complex solution were subjected to measurement of the amount of oxygen absorbed, and as a result, it was found that the molar ratio of the amount of oxygen absorbed to Cu(1) was 1:2 and the resulting complex was an oxygen complex formed according to the following equation:

 (5)

Such an oxygen complex has not yet been reported.

This oxygen complex is so stable that oxygen-oxidation of Cu(1) into Cu(2) by means of combined oxygen requires boiling at 100° C. Further the specific feature of this oxygen complex is that the coordinated oxygen is not eliminated even when it is heated or degassed under reduced pressure, that is, the oxygen absorption reaction is irreversible. Thus, after the Cu(1)Cl.hmpa complex solution is contacted with oxygen or air to form the oxygen complex, it is possible to easily remove excess free oxygen by heating or degassing under reduced pressure. Accordingly, in the case of the oxidation reaction of the organic substrate by means of the combined oxygen in the oxygen complex, since it is possible to avoid free unreacted oxygen in the gas phase part of the reactor, the complex is very advantageous in the aspect of safety. Further, since the complex of the present invention selectively absorbs oxygen from air to form all the same oxygen complex as that in the case of pure oxygen, air is sufficient as oxygen source.

On the other hand, when propylene is oxidized into acetone by means of the combined oxygen activated by coordinating with the transition metal compound, as described above, if propylene can be activated in the form of propylene complex, then it will become possible to carry out easily the instant oxidation reaction at lower temperatures and lower pressures.

Thus, next we have made extensive research on complexes of transition metals belonging to platinum group of the group VIII of the Periodic Table. Palladium chloride Pd(2)Cl₂ as a representative example forms a complex wherein two molecules of hmpa are coordinated with Pd(2)Cl₂ as shown in the following equation, and well dissolves therein:

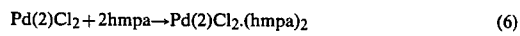
 (6)

If this complex is expressed by the general formula M'm' Xn'.Ll', then m'=1, n'=2 and l'=2 in this case. Further if the central metal ion is Pt(2) or Ir(3) and the anion is SO₄²⁻, resulting complex is Pt(2)SO₄.(hmpa)₂ or Ir(3)₂(SO₄)₃.(hmpa)₂ and m'=1, n'=1 and l'=2 in the former and m'=2, n'=3 and l'=2 in the latter.

It was first studied according to gas absorption method whether or not this Pd(2)Cl₂.(hmpa)₂ complex coordinates with propylene to form a new propylene complex. Namely, with a single hmpa solution system and a Pd(2)Cl₂.(hmpa)₂ complex solution, the amount of propylene absorbed was measured for comparison. As a result, there was no change in the amount between the two, and the absorption amount was the one physically dissolved in hmpa as a solvent. Thus, the Pd(2) complex capable of forming a more stable propylene complex was studied.

As a result, it was found that in a representative example, a system obtained by adding a nitrile as a modifying ligand (an auxiliary complexing agent) to a Pd(2)Cl$_2$.(hmpa)$_2$ complex solution increased the amount of propylene absorbed. Namely, the respective solutions of a hmpa/benzonitrile (PhCN) system and a hmpa/benzonitrile/Pd(2)Cl$_2$ system were subjected to measurement of the amount of gas absorbed, to compare the amounts of propylene absorbed, of the respective solutions. The results are shown in FIG. 2. As seen from this figure, since these systems are non-aqueous, the amount of propylene absorbed is large in the case of the solvent-modifying ligand system (A), but the amount becomes larger in the system (B) where Pd(2) complex is further present; hence it is evident that a stable complex of Pd(2) ion with propylene was formed.

Namely, when acetonitrile (CH$_3$CN) as a representative of nitriles is added to a Pd(2)Cl$_2$.(hmpa)$_2$ complex solution, the following new complex is formed:

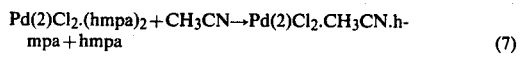

$$Pd(2)Cl_2.(hmpa)_2 + CH_3CN \rightarrow Pd(2)Cl_2.CH_3CN.hmpa + hmpa \quad (7)$$

When propylene is passed therethrough, a stable propylene complex is formed as shown in the following equation:

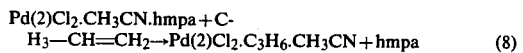

$$Pd(2)Cl_2.CH_3CN.hmpa + C_3H_6\text{—}CH\text{=}CH_2 \rightarrow Pd(2)Cl_2.C_3H_6.CH_3CN + hmpa \quad (8)$$

With such a stable complex, propylene is notably activated.

As described above, propylene coordinated with Pd(2) ion in the form of propylene complex and activated thereby is oxidized by the above-mentioned combined oxygen in the oxygen complex, in a non-aqueous solvent system under mild conditions and at a single stage to produce acetone.

In short, Cu(1)Cl.hmpa complex and Pd(2)Cl$_2$.CH$_3$CN. hmpa complex are dissolved in liquid hmpa which is at the same time a ligand, and oxygen or an oxygen-containing gas such as air is passed through the solution obtained above to form an oxygen complex having an adequate concentration, and if necessary, excess oxygen is removed by heating or degassing, followed by passing propylene through the oxygen complex to form a propylene complex. Propylene activated by this complex formation is oxidized by the combined oxygen in the oxygen complex at a low temperature such as in the vicinity of 40° C. to almost quantitatively form acetone. This oxidation reaction is expressed by the following equation:

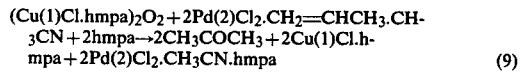

$$(Cu(1)Cl.hmpa)_2O_2 + 2Pd(2)Cl_2.CH_2\text{=}CHCH_3.CH_3CN + 2hmpa \rightarrow 2CH_3COCH_3 + 2Cu(1)Cl.hmpa + 2Pd(2)Cl_2.CH_3CN.hmpa \quad (9)$$

In the present invention, in such a manner, propylene coordinated with Pd(2) complex and activated thereby is oxidized by oxygen molecule coordinated with Cu(1) complex and activated thereby to form acetone; hence there is no change in the valences of the central metals of the complexes. Thus, the instant production process is entirely different in mechanism from a process utilizing an oxidation reaction by way of Pd(2) ion and water or the like process as in conventional processes, and has a great advantage that it is possible to repeat a procedure of separating the resulting product from the catalyst solution by means of an operation such as distillation after completion of the reaction, thereafter again passing air through the catalyst solution and then passing propylene through the resulting solution to regenerate the oxygen complex and the propylene complex according to the equations (5) and (8) and also produce acetone according to the equation (9). In addition, even when a mixed gas of propylene with oxygen in the range outside the explosion limit is passed, the same effectiveness can be obtained. Further, since oxygen and propylene as reaction substrates are activated, it is possible to attain a reaction rate superior to those of the prior art under the atmospheric pressure at a temperature as low as about 40° C. Still further, since the reaction is carried out under mild conditions, the amount of byproducts is small and the selectivity can be improved, as described later in Examples.

As M$_m$X$_n$ in the complex catalyst (M$_m$X$_n$.L$_l$) capable of forming the oxygen complex in the composite catalyst system of the present invention, salts of Cu(1), Ag(1) of the group I, Ti(3), Zr(4) of the group IV, V(3), Nb(3) of the group V, Cr(3), Mo(3), W(3) of the group VI, Mn(2) of the group VII, and Fe(2), Co(2) of the group VIII of the Periodic Table are preferable, and among these, halides of Cu(1), Ti(3) and V(3) are particularly preferable. As for the ligand L, organic phosphorus compounds represented by triphenylphosphine oxide, hexamethylphosphoramide, mono, di- and triesters formed by the reaction of phosphoric acid with methanol, ethanol or the like, and dimethyl methylphosphonate, methyl dimethylphosphinate, each as derivatives of phosphoric acid, and mono-, di- and triesters formed by the reaction of phosphorous acid with methanol, ethanol or the like, phenylphosphinous acid esters, dimethylphosphinic acid esters, triethylphosphine, triphenylphosphine, etc., each as phosphorous acid derivatives, etc. are preferable, and among these, hexamethylphosphoramide (hmpa) is particularly preferable.

On the other hand, as M'$_m$'X$_n$' in the complex catalyst (M'$_m$'X$_n$'.L'$_l$'L$_l$) capable of forming the propylene complex, salts of lower valence ions of transition metals belonging to platinum group of the group VIII are preferable, and among these, halides of Pd(2), Pt(2) or Ir(3) are particularly preferable. As the ligand L', nitriles such as acetonitrile, propionitrile, benzonitrile, tolunitrile, etc., and as the ligand L the above organic phosphorus compounds. Also suitable as L' organic fluorine compounds such as fluorinated toluene, benzotrifluoride, etc. are preferable.

As solvents in the case where the reaction is carried out in solution state, those which dissolve the composite catalyst and at the same time is easily separable from the resulting acetone (b.p. 56° C./760 mmHg) are preferable. Examples of such solvents are at least one kind selected from various solvents such as n-hexane, toluene, cyclohexane, methyl isobutyl ketone, cyclohexanone, ethanol, ethylene glycol, butyl acetate, propylene carbonate, chloroform, chlorobenzene, pyridine, tetrahydrofuran, etc. and mixtures thereof. Further in the case where the ligand L or L' is liquid, it is possible to use itself as solvent at the same time.

Further, it is also possible to have the composite catalyst supported on a porous carrier such as active carbon, silicates, porous glass, polymers having a macroreticular structure, etc. and oxidize propylene into acetone by means of the combined oxygen in the oxygen complex.

If the reaction temperature is loo low, the reaction rate is also low; hence temperatures of 40° C. or higher are preferable and those of 60°~80° C. are particularly preferable.

As to the reaction pressure, the higher the pressure, the higher the oxygen absorption rate, and the larger the amount of propylene in the solution and also the higher the concentration of activated propylene, but a sufficient reaction rate is obtained even under the atmospheric pressure.

In the present invention, when a basic solvent such as sulfolane, dimethylsufolane, dimethylsulfoxide, dimethylformamide, trimethylmethane, etc. is added to the catalyst solution or used as a solvent for the complex itself, it is possible to notably promote the acetone formation reaction.

In addition, although the reaction of the present invention is carried out in a non-aqueous system, the reaction may be carried out in the presence of water in an amount in the range where no precipitate is formed.

A novel complex, its characteristics and examples of production reaction using the complex have been described above. Next the present invention will be described in more detail by way of Examples. The values of gas volume therein is based on the standard state.

EXAMPLE 1

Into a 500 ml capacity test tube with ground stopper were fed cuprous chloride (Cu(1)Cl) (5 g, 50 mmols) and hmpa (325 g) to prepare a Cu(1)Cl.hmpa complex solution (330 ml). Further, into another 500 ml test tube with ground stopper were fed palladium chloride (Pd(2)Cl$_2$) (1.3 g, 7 mmols) and acetonitrile (130 g) to prepare a Pd(2)Cl$_2$.(CH$_3$CN)$_2$ complex solution (170 ml). Both the solutions were then transferred into a 1 l capacity reactor to prepare a complex catalyst solution (Cu(1)Cl.hmpa/Pd(2)Cl$_2$.CH$_3$CN.hmpa/hmpa.CH$_3$CN system) (500 ml) containing 0.1 mol/l of Cu(1)Cl and 0.015 mol/l of Pd(2)Cl$_2$.

Air was passed through the solution at 25° C. under the atmospheric pressure. As a result, oxygen (340 ml, 14 mmols) was apparently absorbed, but thereafter when nitrogen gas was passed, oxygen in the gas phase part in the reactor and oxygen physically dissolved in the solution were removed. However, oxygen of 260 ml was present in the solution in the form of oxygen complex (0.011 mol/l), and elimination of oxygen from this combined oxygen in the oxygen complex was not observed even by way of heating, degassing or the like; thus it was confirmed that the oxygen absorption by the oxygen complex formation was irreversible.

After these operations, propylene (1 l) was passed at 25° C. under the atmospheric pressure. As a result, 700 ml was absorbed in the solution and the propylene concentration in the solution was 0.06 mol/l. Just thereafter, the solution was heated to 60° C. and reaction was carried out for 30 minutes, followed by analyzing the resulting product according to gas chromatography. As a result, acetone (0.51 g, 8.8 mmols) was formed. The reaction of the propylene complex with the oxygen complex is carried out according to the above equation (9) and in this Example, the propylene complex is present in excess of the oxygen complex; hence the amount of acetone formed is regulated by the concentration of the oxygen complex. Thus, the acetone yield was 80% based on the combined oxygen in the oxygen complex.

EXAMPLE 2

Example 1 was repeated except that the reaction temperature was 40° C. and 90° C., to carry out the reaction for 30 minutes. As a result, acetone was formed in amounts of 0.31 g (5.3 mmols) and 4.3 g (7.4 mmols), respectively, and the acetone yield was 48% in the case of 40° C. and 67% in the case of 90° C. Particularly in the case of the reaction temperature of 90° C., elimination of propylene into the gas phase part of the reactor was notably confirmed, and it was found that if the reaction temperature is uselessly raised, the concentration of the propylene complex in the solution lowers although the oxidation rate of propylene increases, to reduce the acetone yield.

In addition, by raising the pressure, it was possible to keep the propylene concentration in the solution constant even when the temperature was raised.

EXAMPLE 3

Example 1 was repeated except that acetonitrile was replaced by benzonitrile. As a result, acetone (0.57 g, 9.9 mmols) was formed, and by changing acetonitrile to benzonitrile, the acetone yield increased from 80% in the case of acetonitrile up to 90%.

EXAMPLE 4

Example 3 was repeated except that the reaction temperature was 40° C. The acetone yield reached 85%.

EXAMPLE 5

Example 1 was repeated in the operation except that air was replaced by pure oxygen. As a result, no significant difference was observed in the concentration of the oxygen complex and that of the propylene complex in the solution. Further, the reaction was carried out under the same conditions as in Example 1. The acetone yield was 82%. Thus, in the present invention, the oxygen source is unnecessary to be pure oxygen, but cheap air may be sufficient.

EXAMPLE 6

Reaction was carried out under the same composition and conditions as those in Examples 1 and 3 except that the amount of hmpa was 50 g (0.3 g mol) and that of benzonitrile was 8 g (0.1 mol) and further sulfolane (240 g, 2.0 mols) was added. Acetone (0.63 g, 10.8 mmols) was formed. This amount corresponds to 98% in terms of the yield based on the combined oxygen in the oxygen complex. Further, the amount of byproducts was also below the detection limit. It is evidenced that basic solvents represented by sulfolane are very effective for improving the yield.

EXAMPLE 7

The same operation and reaction as in Example 6 were carried out except that Pd(2)Cl$_2$ was replaced by Pt(2)Cl$_2$ (8 g, 0.03 mol). The acetone yield was 99%.

EXAMPLE 8

Reaction was carried out under the same conditions as in Example 6 except that Cu(1)Cl was replaced by cuprous bromide (Cu(1)Br). The acetone yield was 96%. Further, when Cu(1)Cl was replaced by cuprous iodide (Cu(1)I), the acetone yield was 97%.

EXAMPLE 9

Reaction was carried out as in Example 7 except that Pt(2)Cl$_2$ was replaced by Pt(2)Br$_2$ and further, Cu(1)Cl, by Cu(1)Br. The acetone yield was 97%.

EXAMPLE 10

The same operation as in Example 6 was carried out except that benzonitrile was replaced by benzotrifluoride. The acetone yield was 93%.

EXAMPLE 11

Reaction was carried out as in Example 3 except that hmpa was used in 85 g and toluene (275 g) was added as solvent. The acetone yield was 92%, that is, almost the same as in Example 3.

EXAMPLE 12

In Example 6, air and propylene outside the explosion limit were at the same time passed through the catalyst solution, at a rate of amount of gas passed/amount of reaction solution of 30 h$^{-1}$. 76% of propylene was oxidized into acetone.

EXAMPLE 13

In Example 6, Cu(1)Cl, Pd(2)Cl$_2$, hmpa, benzonitrile and sulfolane were at the same time added to the reactor. As a result, a uniform solution was obtained. Further, reaction was carried out as in Example 12. No significant difference was observed in the conversion of propylene into acetone. Thus, it is apparent that in the instant production process, the stepwise operation as shown in Example 1 is not always required.

EXAMPLE 14

The same operation as in Example 6 was carried out except that Cu(1)Cl was replaced by V(3)Cl$_3$ and a catalyst solution (500 ml) containing 0.1 mol/l of V(3)Cl$_3$ and 0.015 mol/l of Pd(2)Cl$_2$ was prepared. As a result, an oxygen complex of 0.014 mol/l (160 ml in terms of combined oxygen) and a propylene complex of 0.057 mol/l were formed. Thereafter these were reacted together at 40° C. for 30 minutes to obtain acetone (0.32 g, 5.5 mmols). The acetone yield based on combined oxygen was 39%.

EXAMPLE 15

The same operation as in Example 14 was carried out except that V(3)Cl$_3$ was replaced by Ti(3)Cl$_3$ and the amount of Ti(3)Cl$_3$ was 0.1 mol/l. As a result an oxygen complex of 0.036 mol/l and a propylene complex of 0.057 mol/l were formed. They were reacted together under the same conditions as in Example 14. The acetone yield was 42%.

EXAMPLE 16

Beads of a macroreticular type styrene-divinylbenzene copolymer (particle diameter, 1 mm$\phi$; specific surface area, 700~800 m$^2$/g; Amberlite XAD-4 manufactured by Organo Co.) (50 ml) were impregnated with the catalyst solution containing the oxygen complex of the composition shown in Example 6, followed by filtering by suction to obtain a particulate catalyst. This catalyst was filled in a hard glass reaction tube of 20 mm$\phi$ in inner diameter, followed by heating to 60° C., then passing propylene at a rate of 1 l/min. (SV: 1,200 h$^{-1}$) and analyzing the resulting product in the exit gas according to gas chromatography. As a result, the product was acetone alone and the acetone yield based on propylene was 4% since the start of the reaction till the succeeding two hours. Thereafter when the exit gas was recycled, the acetone yield based on the oxygen complex reached 70%. Further, propylene feed was once stopped and air was passed to regenerate combined O$_2$ consumed by the reaction, followed by again repeating the oxidation experiment under the above conditions, to obtain similar results.

From the foregoing, it was clarified that even when the complex of the present invention was supported on a porous carrier, the reaction by means of the combined oxygen in the oxygen complex advanced. In addition, as the carrier, porous carriers such as silicates, active carbon, porous glass, etc. are usable, and as the treating method after the impregnation, various methods such as passing of heated gas, low temperature calcination are employable in addition to the above filtering by suction.

COMPARATIVE EXAMPLE 1

Preparation of the catalyst solution and operation were carried out as in Examples 3 and 11 except that nitrile or organic fluorine compound was not added. As a result, the acetone yields were all less than 0.1%. From this result it was evidenced that nitriles and organic fluorine compounds as a modifying ligand modified the physical properties of coordinated metal ions to form a stable propylene complex and contributed greatly to the activation of propylene.

COMPARATIVE EXAMPLE 2

Into the same reactor as in Example 1 were fed Pd(2)Cl$_2$ (1.3 g) and hmpa (325 g) to prepare a hmpa solution of Pd(2)Cl$_2$.(hmpa)$_2$ complex. No oxygen was passed through this solution, and propylene was passed in the same operation as in Example 1, followed by reacting under the same conditions (60° C., 30 minutes). As a result, propylene was entirely not oxidized. Further no precipitate of metal palladium (Pd(0)) was formed; thus it was evidenced that oxidation by means of Pd(2) ion did not occur in the non-aqueous solvent system.

COMPARATIVE EXAMPLE 3

To the complex solution prepared in Comparative example 2 was added Cu(1)Cl (5 g) to prepare a catalyst solution of Cu(1)Cl/Pd(2)Cl$_2$/hmpa, followed by carrying out the same operation and reaction as in Comparative example 2. As a result, propylene oxidation was utterly not observed. It was evidenced that it was necessary to pass oxygen to thereby form the oxygen complex.

COMPARATIVE EXAMPLE 4

Into the complex solution prepared in Comparative example 3 was added benzonitrile, followed by carrying out the same operation and reaction as in Comparative example 2. In this case, too, since oxygen was not passed, propylene oxidation was not observed.

COMPARATIVE EXAMPLE 5

In Comparative example 2, oxygen was passed, but propylene was utterly not reacted. This evidences that oxidation reaction by means of free oxygen does not occur in the instant system.

From the above Comparative examples 2 and 3, it is evident that the present invention is entirely different from the process of producing acetone from propylene, using as catalyst, the Pd(2)Cl-Cu(2)Cl redox system.

Further, into the catalyst solution containing the propylene complex in Comparative example 4 was passed oxygen. As a result, acetone was formed with the same high efficiency as in the above respective Examples.

From the foregoing it is evidenced that the present invention is different from the prior art and directed to a new process wherein the combined propylene activated by formation of the propylene complex is oxidized by combined oxygen activated by formation of oxygen complex to produce acetone.

According to the present invention, propylene does not contact directly with oxygen, each in the form of free molecule, but propylene and oxygen each coordinated with a transition metal ion and activated thereby are reacted together by means of a specified composite catalyst system, whereby it is possible to produce the objective acetone at low temperatures in the vicinity of room temperature, under the atmospheric pressure, selectively and with a high yield. Further, according to the production process of the present invention, since the amount of byproducts is small, the production step including the subsequent purification is simplified. In addition, since oxygen is selectively absorbed even when air is used as an oxygen source, all the same effectiveness as in the case of use of pure oxygen is obtained. Still further, since the oxygen absorption is irreversible, it is possible to easily remove excess free oxygen after formation of the oxygen complex; hence the process is very advantageous in the aspect of safety.

What we claim is:

1. A process for producing acetone by oxygen-oxidizing propylene in the presence of a metal complex catalyst, which process comprises employing a composite catalyst containing as the metal complex catalyst, a first complex (Mm Xn.Ll) capable of forming an oxygen complex by coordination of the complex with oxygen and a second complex (m'm' Xn'.L'l' Ll) capable of forming a propylene complex by coordination of the complex with propylene, wherein M is a transition metal belonging to group I, groups IV–VII and the iron group in group VIII of the Periodic Table; X, and anion; L, an organic phosphorus compound selected from the group consisting of triphenylphosphine oxide, hexamethylphosphoramide, mono-, di- and triesters formed by the reaction of phosphoric acid with methanol and ethanol, dimethyl methylphosphonate, methyl dimethylphosphinate, mono-, di- and triesters formed by the reaction of phosphoric acid with methanol and ethanol, phenylphosphinous acid esters, dimethylphosphinic acid esters, triethylphosphine and triphenylphosphine; M', a transition metal belonging to the platinum group in group VIII of the Periodic Table; L', a coordinating compound selected from the group consisting of acetonitrile, propionitrile, benzonitrile, tolunitrile, fluorinated toluene, benzotrifluoride; m, m', n and n', each a number determined by valences of the above transition metals and the above anion; and l and l', each the number of ligands.

2. A process for producing acetone according to claim 1, wherein the first complex is Cu(1) Cl.hmpa and further wherein the second complex is Bd(2) Cl$_2$.CH$_3$CN.hmpa.

3. A process for producing acetone according to claim 1 wherein said m, m', n, n', l and l' are each in the range of 1 to 4.

4. A process for producing acetone according to claim 1 wherein said X is at least one anion selected from the group consisting of Cl$^-$, Br$^-$, I$^-$, CH$_3$OO$^-$, BF$_4^-$, PF$_6^-$ and SO$_4^{2-}$.

5. A process for producing acetone according to claim 1, wherein as the solvent for said complex capable of forming an oxygen complex and said complex capable of forming a propylene complex, at least one compound selected from the group consisting of aliphatic, alicyclic and aromatic hydrocarbons, oxygen-containing organic compounds, organic halogen compounds and nitrogen-containing compounds is used.

6. A process for producing acetone according to claim 1, wherein said ligands L and L' are each liquid and these ligands themselves are each at the same time used as a solvent for said complex capable of forming an oxygen complex and said complex capable of forming a propylene complex.

7. A process for producing acetone according to claim 1, wherein an oxygen-containing gas and propylene are passed through the solution of said composite catalyst to form an oxygen complex and a propylene complex and these two are reacted together.

8. A process for producing acetone according to claim 1, wherein a porous carrier is impregnated with the solution of said composite catalyst, an oxygen-containing gas and propylene are passed through the resulting material, and propylene is oxidized with the combined oxygen in said oxygen complex.

9. A process for producing acetone according to claim 1, wherein at least one basic (electron-donative) compound selected from the group consisting of sulfolane, dimethylsulfolane, dimethylsulfoxide and dimethylformamide is added to said composite catalyst.

10. A process according to claim 1, wherein the transition metal M is selected from the group consisting of Cu(1) and Ag of Group I, Ti(3) and Zr(4) of Group IV, V(3) and Nb(3) of Group V, Cr, Mo and W of Group VI, Mn of Group VIII, and Fe, Co and Ni of Group VIII of the Periodic Table.

11. A process according to claim 10, wherein the transition metal is selected from the group consisting of Cu(1), Ti(3) and V(3).

12. A process according to claim 1, wherein the transition metal M' is selected from the group consisting of Pd(2), Pt(2) and Ir(3).

13. A process according to claim 1, wherein the ligand L' is nitrile.

14. A process according to claim 1, wherein the organic phosphorus compound is hexamethylphosphoramide.

15. A process for producing acetone by oxygen-oxidizing propylene comprising:
dissolving a first complex (Mm Xn.hmpa) and a second complex (M'm' Xn'.L'l' hmpa) in liquid hmpa wherein M is a transition metal belonging to the group I, groups IV–VII and the iron group in group VIII of the Periodic Table; X, and ion: M', a transition metal belonging to the platinum group in group VIII of the periodic table; L', a coordinating compound selected from the group consisting of acetonitrile, propionitrile, benzonitrile, tolunitrile, fluorinated toluene and benzotrifluoride; m, m', n, and n', each a number determined by the valences of the above transition metals and the above anion; and l', the number of the coordinating compound; passing at least one of oxygen and an oxygen containing gas through the hmpa solution containing the dissolved complexes to form an oxygen complex with the first complex;

passing propylene through the hmpa solution to form a propylene complex with the second complex;

heating the hmpa solution containing the oxygen complex and and propylene complex to a temperature in the range of 40° to 90° C. to oxidize the propylene with the oxygen to produce acetone.

16. A process according to claim 15, wherein the temperature is in the range of 60° to 80° C.

17. A process according to claim 5, wherein the solvent is at least one of n-hexane, toluene, cyclohexane, methyl isobutyl ketone, cyclohexanone, ethanol, ethylene glycol, butyl acetate, propylene carbonate, chloroform, chlorobenzene, pyridine, tetrahydrofuran and mixtures thereof.

18. A process according to claim 15, wherein hmpa solution containing the first complex and the second complex contains 0.1 mol per liter of the first complex and 0.015 mol per liter of the second complex;

air is passed through the solution at 25° C. under atmospheric pressure;

propylene is passed through the hmpa solution at 25° C. under atmospheric pressure;

and further wherein the thus created solution is heated to 60° C. for 30 minutes.

19. A process according to claim 18, wherein 5 grams of Cu(1) Cl and 50 grams of hmpa by weight is used to prepare the first complex, and 1.3 grams of Pd(2) Cl$_2$ and 8 grams of benzonitrile is used to prepare the second complex, and further wherein 240 grams of sulfolane is used to prepare the hmpa solution containing the first complex and the second complex.

* * * * *

UNITED STATES PATENT AND TRADEMARK OFFICE
CERTIFICATE OF CORRECTION

PATENT NO. : 4,605,776
DATED : August 12, 1986
INVENTOR(S) : Kamiguchi, et al.

It is certified that error appears in the above—identified patent and that said Letters Patent is hereby corrected as shown below:

Column 11, line 40, delete "m'm'Xn'.L'l'L1"

and substitute --M'm'Xn'.L'l'L1--.

Signed and Sealed this

Twenty-fifth Day of August, 1987

*Attest:*

DONALD J. QUIGG

*Attesting Officer*     *Commissioner of Patents and Trademarks*